US010925516B2

(12) United States Patent
Pallas Areny et al.

(10) Patent No.: US 10,925,516 B2
(45) Date of Patent: Feb. 23, 2021

(54) METHOD AND APPARATUS FOR ESTIMATING THE AORTIC PULSE TRANSIT TIME FROM TIME INTERVALS MEASURED BETWEEN FIDUCIAL POINTS OF THE BALLISTOCARDIOGRAM

(71) Applicant: UNIVERSITAT POLITECNICA DE CATALUNYA, Barcelona (ES)

(72) Inventors: Ramon Pallas Areny, Barcelona (ES); Ramon Casanella Alonso, Barcelona (ES); Joan Gomez Clapers, Barcelona (ES)

(*) Notice: Subject to any disclaimer, the term of this patent is extended or adjusted under 35 U.S.C. 154(b) by 509 days.

(21) Appl. No.: 15/765,293

(22) PCT Filed: Sep. 30, 2016

(86) PCT No.: PCT/ES2016/070692
§ 371 (c)(1),
(2) Date: Apr. 2, 2018

(87) PCT Pub. No.: WO2017/055670
PCT Pub. Date: Apr. 6, 2017

(65) Prior Publication Data
US 2018/0279917 A1 Oct. 4, 2018

(30) Foreign Application Priority Data
Oct. 2, 2015 (ES) ................ ES201531414

(51) Int. Cl.
A61B 5/02 (2006.01)
A61B 5/11 (2006.01)
(Continued)

(52) U.S. Cl.
CPC ............ A61B 5/1102 (2013.01); A61B 5/02 (2013.01); A61B 5/021 (2013.01);
(Continued)

(58) Field of Classification Search
CPC .. A61B 5/11; A61B 5/021; A61B 5/02; A61B 5/02125; A61B 5/1102; A61B 5/0402; A61B 5/0295
See application file for complete search history.

(56) References Cited

U.S. PATENT DOCUMENTS

2013/0310700 A1* 11/2013 Wiard ................. A61B 5/0402
600/485
2015/0018637 A1* 1/2015 Chen .................... A61B 5/0295
600/301
2016/0081563 A1* 3/2016 Wiard .................... A61B 5/029
600/485

FOREIGN PATENT DOCUMENTS

WO WO2012103296 A2 8/2012
WO WO2013109188 A1 2/2013
(Continued)

OTHER PUBLICATIONS

Chang-Sei, et al., "Ballistocardiogram as Proximal Timing Reference for Pulse Transit Time Measurement: Potential for Cuffless Blood Pressure Monitoring," IEEE Trans Biomed Eng Nov. 2015;62(11):2657-64. Epub Jun. 2, 2015. (Year: 2015).*
(Continued)

Primary Examiner — Eric J Messersmith
(74) Attorney, Agent, or Firm — Eugenio J. Torres-Oyola; Victor M. Rodriguez-Reyes; Rafael Rodriguez-Muriel

(57) ABSTRACT

A method and apparatus is proposed to estimate the aortic pulse transit time (PTT) from only time intervals measured between fiducial points of the longitudinal ballistocardiogram (BCG) without the need to apply any sensor to the area where the arrival of the arterial pulse waveform is to be detected. From the longitudinal BCG of a subject, which can be obtained by means of sensors integrated in a single element with which the subject's body comes into contact, two fiducial points of the BCG waveform are detected in
(Continued)

which one of the points is associated with the arrival of the arterial pulse wave to a zone proximal to the heart and the other is associated with the arrival of said arterial pulse wave to a distal zone, respectively. From the time interval between the two points, an estimate of the aortic (carotid-femoral) PTT is provided either directly or through a process of previous calibration.

15 Claims, 3 Drawing Sheets

(51) Int. Cl.
  *A61B 5/021*  (2006.01)
  *A61B 5/0295*  (2006.01)
  *A61B 5/0402*  (2006.01)
  *A61B 5/0456*  (2006.01)
  *A61B 5/00*  (2006.01)

(52) U.S. Cl.
  CPC ............ *A61B 5/02125* (2013.01); *A61B 5/11* (2013.01); *A61B 5/0295* (2013.01); *A61B 5/0402* (2013.01); *A61B 5/0456* (2013.01); *A61B 5/7246* (2013.01)

(56) References Cited

FOREIGN PATENT DOCUMENTS

| WO | WO2013128364 A1 | 9/2013 |
|----|-----------------|--------|
| WO | WO2014157896 A1 | 10/2014 |
| WO | WO201503695 A1 | 3/2015 |

OTHER PUBLICATIONS

C. vLachopoulos, K. Aznaouridis, and C. Stefanadis, "Prediction of Cardiovascular Events and All-cause Mortality With Arterial Stiffness: a Systematic Review and Meta-analysis", Journal American College Cardiology, vol. 55, No. 13, pp. 1318-1327, Mar. 2010.

L.M. Van Bortel, S. Laurent, P. Boutouyrie, P. Chowienczyk, J.K. Cruickshank, et al., "Expert Concensus Document on the Measurement of Aortic Stiffness in Daily Practice Using Carotid-femoral Pulse Wave Velocity, ", Journal Hypertension, vol. 30, No. 3, pp. 445-448, Mar. 2012.

D. Buxi, J.M. Redouté, and M.R. Yuce, "A Survey on Signals and Systems in Ambulatory Blood Pressure Monitoring Using Pulse Transit Time," Physiological Measurements, DOI 10.1088/0967-3334/36/3/R1.

O.T. Inan, P.F. Migeotte, K.-S. Park, M. Etemadi, K. Tavakolian, et al., "Ballistocardiography and Seismocardiography: A Review of Recent Advances," IEEE Journal of Biomedical Health and Informatics, DOI 10.1109/JBHI.2014.2361732.

A. Akhbardeh, B. Kaminska y K. Tavakolian, BSeg++: A modified Bling Segmentation Method for Ballistocardiogram Cycle Extraction, Annual International Conference of the IEEE Engineering in Medicine and Biology Society (EMBC), 2007, pp. 1896-1899.

R. Casanella, On Time Interval Measurement Using BCG, 34th Annual International Conference of the IEEE EMBS San Diego, California USA, Aug. 28-Sep. 1, 2012, pp. 5034-5037.

\* cited by examiner

METHOD AND APPARATUS FOR ESTIMATING THE AORTIC PULSE TRANSIT TIME FROM TIME INTERVALS MEASURED BETWEEN FIDUCIAL POINTS OF THE BALLISTOCARDIOGRAM

CROSS-REFERENCE TO RELATED APPLICATIONS

This application is the entry into national phase of International Application No. PCT/ES2016/070692, filed on Sep. 30, 2016, the content of which is hereby incorporated by reference in its entirety, which claims the benefit of Spanish Patent Application No. P20153144, filed on Oct. 2, 2015, the entire disclosure of which is incorporated herein by reference.

FIELD OF THE INVENTION

The present invention relates in general to systems for measuring physiological parameters through physical methods and, in particular, to a method and apparatus for estimating the aortic pulse transit time from time intervals measured between fiducial points exclusively measured on the ballistocardiogram (BCG).

BACKGROUND OF THE INVENTION

Pulse Transit Time (PTT), generated by the ejection of blood from the heart to the arterial system, is a very important parameter for diagnosing the state of the cardiovascular system. It is defined as the time interval between the arrival of the pulse wave at a point proximal to the heart and the arrival at another distal point. Using PTT can be evaluated, for example, arterial elasticity, which is an increasingly accepted indicator for predicting the risk of cardiovascular disease. Arterial elasticity has been associated to the presence of cardiovascular risk factors and arteriosclerotic disease, and its suitability for predicting risk of future cardiovascular events such as myocardial infarction, stroke, revascularization or aortic syndromes, among others, has been widely corroborated, as described in the document by C. Vlachopoulos, K. Aznaouridis, and C. Stefanadis, "Prediction of Cardiovascular Events and All-cause Mortality With Arterial Stiffness: a Systematic Review and Meta-analysis," *Journal American College Cardiology*, vol. 55, no. 13, pp. 1318-27, March 2010.

The degree of elasticity of an artery is normally evaluated from the propagation speed of the blood pulse wave, the so-called pulse wave velocity (PWV), according to the Moens-Korteweg's formula, $$PWV = \sqrt{\frac{Eh}{2r\rho}},$$

where E is the elastic modulus of the artery, h is the width of the arterial wall, r is the arterial radius and $\rho$ is the blood density.

The measurement of PWV in the aorta is of the greatest clinical relevance because the aorta and its main branches are responsible for most of the pathophysiological effects derived from arterial stiffness, so that aortic PWV is a good indicator of the state of stiffness of the subject's arteries. Aortic PWV has shown high predictivity of cardiovascular events in several epidemiologic studies, as described in the document by L. M. Van Bortel, S. Laurent, P. Boutouyrie, P. Chowienczyk, J. K. Cruickshank, et al., "Expert Consensus Document on the Measurement of Aortic Stiffness in Daily Practice Using Carotid-femoral Pulse Wave Velocity," *Journal Hypertension*, vol. 30, no. 3, pp. 445-448, March 2012.

A common method to non-invasively measure the PWV in an artery is from the PTT in said artery, according to $$PWV = \frac{D}{PTT},$$

where D is the distance between the proximal and distal sites considered. On the aorta, the PWV is usually measured between the carotidal site, located in the medial area of the anterior edge of the sternocleidomastoid muscle, and the femoral site, located at the medial area of the inguinal crease. Arteries in such sites are superficial and easily accessible by using a sensor in direct contact to the skin, and the PTT between them properly reflects the aortic PTT since it includes most of the aortic and aortic-iliac propagation.

Another parameter that can be measured from the elasticity of an artery is blood pressure, as the modulus of elasticity is related to changes in mean blood pressure P according to $$E = E_0 e^{kP},$$

where $E_0$ is the elasticity modulus of the artery at a reference mean arterial pressure and k is a constant that depends on the artery and whose valor is comprised between 0.016 mmHg$^{-1}$ y 0.018 mmHg$^{-1}$. Changes in arterial blood pressure and absolute values of arterial blood pressure can be estimated from PTT measurements in the aorta or in other arteries by using different calibration methods, as described, for example, in the document by D. Buxi, J. M. Redouté, and M. R. Yuce, "A Survey on Signals and Systems in Ambulatory Blood Pressure Monitoring Using Pulse Transit Time," *Physiological Measurements*, DOI 10.1088/0967-3334/36/3/R1.

The common procedure for measuring aortic PTT requires preparation (to expose, clean, place the sensors and connect the cables) of the carotidal and femoral sites to detect in each of them the arrival of the blood pressure pulse by means of, for instance, a photoplethysmograph (PPG) or an impedance plethysmograph (IPG) that detect local volume changes due to the arrival of the pressure pulse, or by means of an arterial tonometer that measures the pressure that a superficial artery exerts to a force sensor in close contact to it. These and other sensors able to detect the arrival of a blood pulse wave to the area where they are placed require skill in their placement, entail slow procedures and become uncomfortable for the subject. In addition, prolonged application of the sensor may cause discomfort to the subject, which makes it inadvisable to take the measurement for long periods of time because of the possible physiological effects of the measurement action.

An alternative method to obtain information about the cardiovascular mechanical activity at the aorta that requires less preparation of the subject is to determine the timing of fiducial points of the ballistocardiogram (BCG), which reflects variations of the gravity center of the human body, either in terms of displacement, speed or acceleration, as a result of the ejection of blood in each heartbeat and the consequent propagation of the blood pulse wave through the arterial tree. The BCG can be obtained from different systems, some of them implemented with sensors embedded in daily use objects such as bodyweight scales, chairs or beds, as it is described in the document by O. T. Inan, P. F. Migeotte, K.-S. Park, M. Etemadi, K. Tavakolian, et al., "Ballistocardiography and Seismocardiography: a Review of Recent Advances," *IEEE Journal of Biomedical Health and Informatics*, DOI 10.1109/JBHI.2014.2361732, or embedded in clothing such as shoes or socks. In such systems, measurements become faster and more comfortable, and in some implementations can be performed for long periods without causing any trouble to the subject because, instead of placing sensors at specific sites to detect the arrival of the pressure wave, it is the body of the subject that naturally contacts an element (platform, bodyweight scale, chair, bed, garment) with the sensors integrated in it.

For the time being, the timing of fiducial points of the BCG have been used to detect the arrival of the blood pulse wave to proximal sites respect to the heart due to the relationship between the BCG and the onset of blood ejection into the aorta. For instance, in patent US 20130310700 A1 it is proposed to use fiducial points of a BCG obtained from a system embedded into a weighing scale as a proximal timing reference to measure the aortic PTT. However, the method described in said patent requires an additional sensor to detect the arrival of the blood pressure wave to a distal site.

Obtaining proximal and distal temporal information on the same BCG signal would allow the aortic PTT to be measured more quickly and comfortably even over long periods of time, which would be very useful for evaluating arterial elasticity and its derived parameters. The method would also be of great interest to calculate other health indicators that involve the aortic PTT, such as myocardial contractility evaluated from the pre-ejection period (PEP) calculated by subtracting the PTT from the pulse arrival time (PAT).

SUMMARY OF THE INVENTION

The present invention provides a method and apparatus for estimating the aortic pulse transit time (PTT), said method and apparatus being defined in the independent claims. Several preferred embodiments are described in the dependent claims. As used herein and in any appended claims, the term aortic PTT refers to the PTT between the carotidal site, located in the medial area of the anterior edge of the sternocleidomastoid muscle, and the femoral site, located at the medial area of the inguinal crease.

The innovative solution proposed in the present invention is the estimation of aortic PTT from time intervals measured between fiducial points exclusively obtained from the BCG. As this signal is usually obtained by means of sensors integrated in a single element with which the subject's body comes into contact, the use of BCG avoids the need for additional pulse wave sensors and the inconvenience of having to place these sensors in the specific areas where the arrival of the arterial pulse wave is to be detected.

This innovative solution is based on the fact that BCG waves reflect changes in the center of gravity of the human body resulting from the overlapping effects of cardiac ejection and the propagation of the arterial pulse wave. Therefore, it is expected that the earliest points of BCG with respect to cardiac systole are mostly related to events linked to cardiac ejection, while the fiducial points furthest from the start of the signal with respect to cardiac systole are expected to be more influenced by events related to the arrival of the pulse wave to distal areas. Since the aorta is comparatively the artery with the greatest volume of blood and its orientation is longitudinal (parallel to the head-feet axis), it is expected that the waves of longitudinal BCG will be especially influenced by the mechanical activity derived from the propagation of the pulse wave that occurs in this main artery.

As a result, a method is proposed for estimating aortic PTT comprising, first, of detecting two fiducial points of a BCG: a first point plausibly related to the arrival of the pulse wave to areas closer to the heart and a second point later in time plausibly related to the arrival of the pulse wave to more distal areas. The time interval between these two fiducial points is then measured. This interval corresponds, in a first way of obtaining it, directly to the aortic PTT. A second alternative way to obtain this transit time from the time interval measured between the two fiducial points is to calibrate the BCG interval using the aortic PTT obtained simultaneously with one of the known state-of-the-art methods as a reference. Using the relationship obtained in the calibration; in subsequent measurements the aortic PTT can be calculated from the time interval obtained exclusively from the BCG, thus achieving greater accuracy than in the first way proposed, although with a slower and more complex initial procedure.

Applying the proposed method, the inventors have found that, specifically, BCG waves I and J are systematically coincident with the arrival of the pulse wave at the carotid and femoral points, respectively, making the IJ interval particularly suitable for obtaining the aortic PTT directly from it, according to the first proposed method of obtaining it. The use of the second method, based on IJ interval calibration, is also suitable if a more accurate measurement of the aortic PTT is desired.

On the other hand, measured intervals between other arbitrarily chosen longitudinal BCG fiducial points are expected to be equally sensitive to changes in PTT in the aorta, such as the interval between waves I and K, or the interval between waves J and K. However, the different duration of these intervals with respect to the aortic PTT will result in the use of the proposed second method of obtaining the aortic PTT, based on a previous calibration of the relationship between the interval considered and the aortic PTT measured with any of the conventional methods.

Even though an expert using the temporal relationships between the waves of the BCG and the time arrival of the blood pressure pulse to those particular sites of the arterial tree proposed in this invention, could identify visually the fiducial points that belong to a given heartbeat on a BCG recording and manually measure the time interval between them, an optimal implementation of this invention is through an apparatus that contains the means to process a signal to automatically detect a first and a second fiducial point in a BCG signal, the means to calculate the time interval between said fiducial points and to obtain from it the aortic PTT, and the means to communicate said aortic PTT to a user via a display element or to another device. An algorithm that is able to detect and measure the time interval between the I and J waves from the BCG signal solely could be, for instance, that described in the document by A. Akhbardeh, B. Kaminska y K. Tavakolian, "BSeg++: A modified Blind Segmentation Method for Ballistocardiogram Cycle Extraction," *Annual International Conference of the IEEE Engineering in Medicine and Biology Society (EMBC)*, 2007, pp. 1896-1899. Other algorithms that belong to the state of the art rely on an additional cardiovascular signal to provide a more robust timing reference to identify the I wave and the J wave instead of using the BCG solely. For instance, on the previously cited document by Inan et al. (DOI 10.1109/JBHI.2014.2361732) the J wave is identified as the maximum of the BCG signal in a certain time interval after the R wave of the electrocardiogram (ECG). This method is easily replicable from other cardiovascular signals that have better signal-to-noise ratio (SNR) than the BCG and can be unobtrusively obtained from distal sites of the body, such as the PPG, the IPG locally measured, i.e., placed on the target site, or the IPG measured between two limbs.

A major advantage of the invention herein described is that the aortic PTT is obtained by using only fiducial points of the BCG. This makes the measurement easier, faster and more comfortable even for long term measurements than the existing systems that require different cardiovascular signals to obtain at least one of the two fiducial points needed to measure a time interval, or that involve the placement of one or more sensors in the areas between which the PTT is to be measured.

BRIEF DESCRIPTION OF THE DRAWINGS

To complement the description that is being made and in order to provide a better understanding of the features of the invention, a set of drawings is accompanied as an integral part of this description where, with illustrative and not restrictive character, the following has been represented.

DETAILED DESCRIPTION OF VARIOUS PREFERRED EMBODIMENTS

Figure 1:
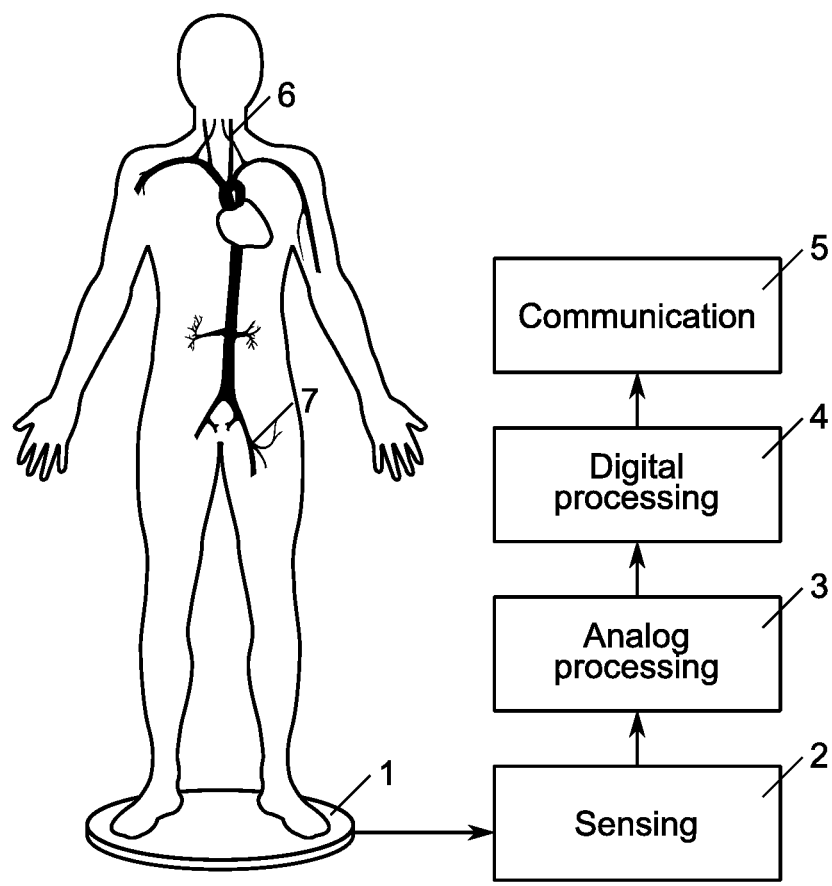
FIG. 1 is a diagram that represents a bodyweight scale able to obtain the BCG and that constitutes the element with which the subject's body contacts in one of the embodiments of the present invention.

In a preferred embodiment of the present invention that is depicted in FIG. 1, a system integrated into a bodyweight scale (1) obtains a longitudinal BCG that reveals the mechanical activity due to cardiac ejection into the aorta, said BCG being obtained from a sensor (2) that consists of the strain gauges already included in the bodyweight scale, where they are used to measure body weight, and an analog signal processing block (3).

From the BCG obtained at the output of the described system, the method for estimating aortic pulse transit time is first to detect two fiducial points in the BCG by digital signal processing: a first point related to the arrival of the arterial pulse wave to more proximal areas, which in this case would correspond to the minimum of wave I, and a second point related to the arrival of the arterial pulse wave to more distal areas, which in this case would correspond to the maximum of wave J. Next, the digital signal processing system (4) being used in this preferred embodiment to detect these fiducial points measures the time interval between them, which in this preferred embodiment is the time interval between the minimum of wave I and the maximum of wave J, called the IJ interval, in each beat. This IJ interval would correspond, in a first way of obtaining it, to the aortic PTT. Finally, the communication module (5) is responsible for communicating the estimated aortic PTT value of the subject through an LCD monitor.

Figure 2:
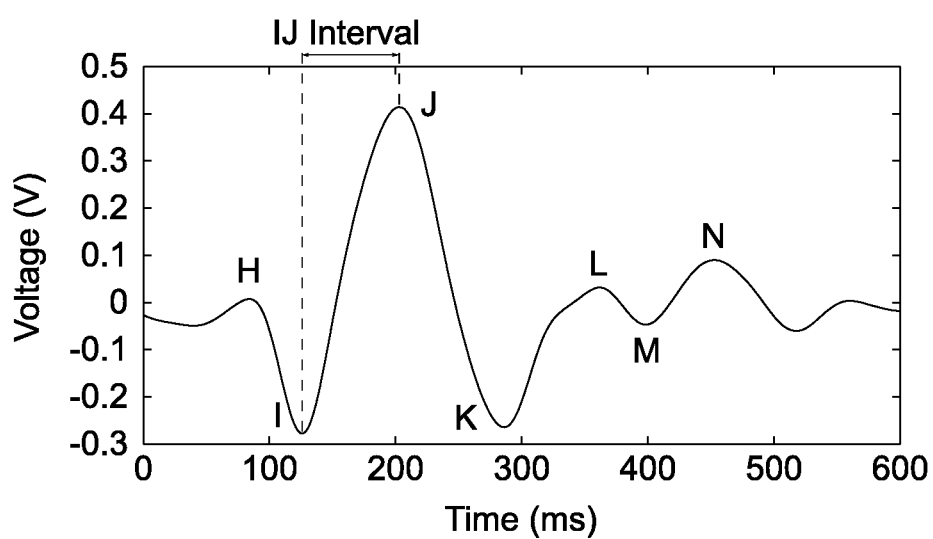
FIG. 2 shows a typical BCG waveform, measured in a standing subject, their main waves: I, J, K, L, and M, which appear at each heartbeat, and the IJ interval. The zero in the abscissa axis coincides with the peak of the ECG R wave, even though this ECG signal is not essential for measuring the IJ interval.
Figure 3:
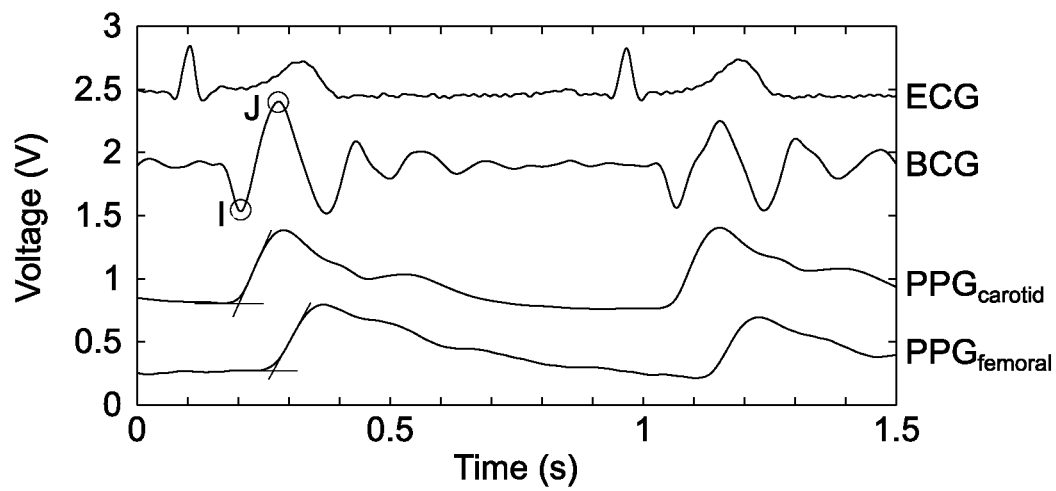
FIG. 3 shows, from top to bottom, an ECG recording (represented in order to ease the interpretation of the present invention even though it is not essential for measuring intervals between fiducial points of the BCG), a BCG recording obtained from a bodyweight scale, a PPG obtained at the carotidal site, and a PPG obtained at the femoral site, all of them simultaneously measured from a same subject.

FIG. 2 shows an example of a BCG record that belongs to a single heart beat and has been obtained from a system embedded in a bodyweight scale; the I wave, J wave, and the IJ interval are annotated. FIG. 3 shows the ECG and BCG tracings simultaneously obtained from the same subject, as well as two tracings obtained from respective PPG sensors placed on the carotidal and femoral sites; the aortic PTT can be measured from these two sensors by placing each on the specific site where the blood pressure pulse must be detected, as usual. This figure illustrates the correspondence between the minimum of the I wave and the foot of the arterial blood pulse at the carotidal site (6), the correspondence between the maximum of the J wave and the foot of the arterial blood pulse at the femoral site (7), and how, consequently, the aortic PTT can be obtained from said two fiducial points by following the method proposed in this preferred embodiment.

Figure 4:
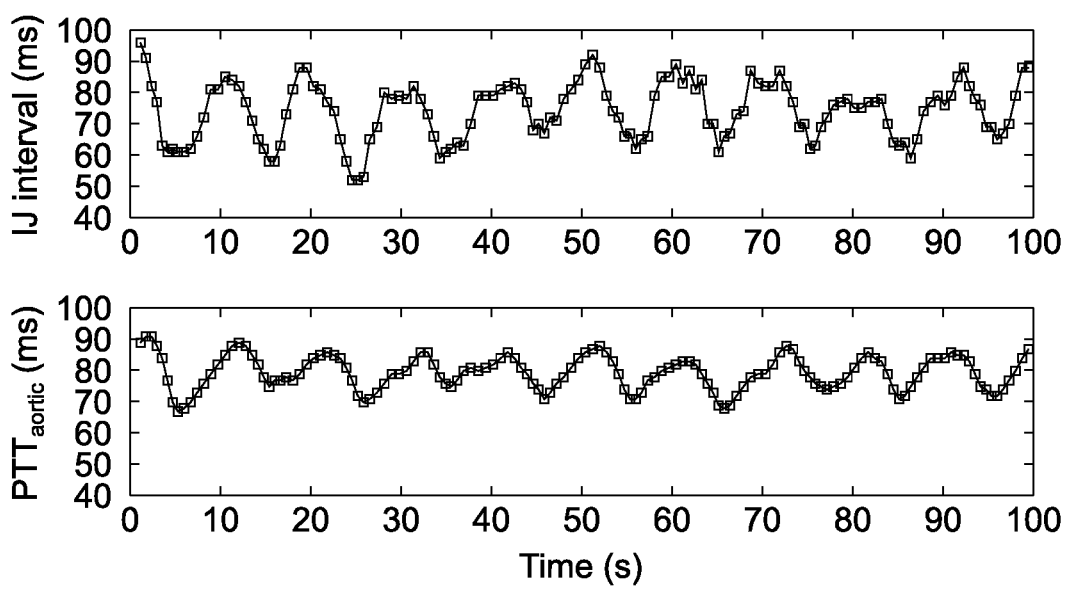
FIG. 4 shows an IJ interval record of the BCG and a carotid-femoral PTT record simultaneously obtained from the same subject while he was performing a paced respiration maneuver in order to modulate arterial stiffness via respiratory-induced blood pressure variations.
Figure 5:
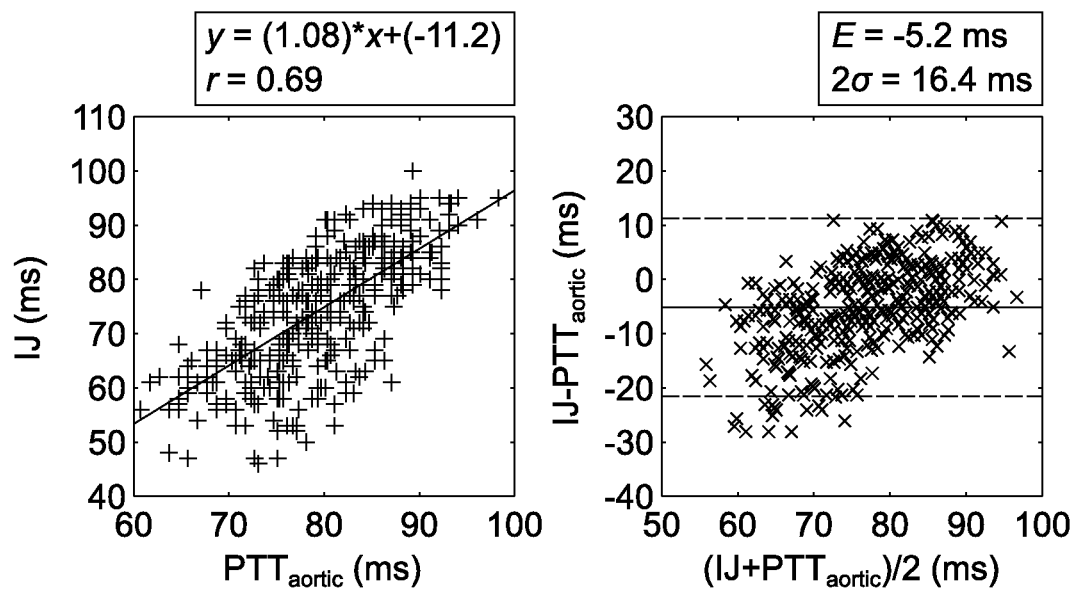
FIG. 5 shows a linear regression analysis and a Bland-Altman analysis of 407 measurements of simultaneous IJ interval and carotid-femoral PTT.

FIG. 4 shows a simultaneous IJ interval tracing, obtained from this preferred embodiment, and aortic PTT tracing measured by using two PPG sensors placed at the carotidal and femoral sites. These two tracings show the correspondence between the IJ interval and the aortic PTT when the subject is performing a paced respiration in order to modulate arterial stiffness via respiration-induced blood pressure changes. FIG. 5 shows the linear regression analysis and Bland-Altman analysis of 407 pairs of IJ interval and aortic PTT measurements obtained from different subjects under paced respiration that further illustrate the correspondence between both parameters. Since the IJ interval duration is similar to the aortic PTT duration and the magnitude of the respiration-induced trends is equivalent, in this preferred embodiment the aortic PTT is estimated as the IJ interval. The difference between intervals (mean-5.2 ms and standard deviation 13.2 ms, as shown in FIG. 5) is attributable to the intrinsic uncertainty of the measurement.

To improve the accuracy of the aortic PTT estimation, a second preferred embodiment of the present invention is proposed using the relationship between the IJ interval and the aortic PTT previously determined through calibration. In this preferred embodiment, a linear regression between the IJ interval and the aortic PTT is calculated, obtained from the simultaneous measurement of both intervals in a target group or a representative part of it, which allows a more accurate estimation of the aortic PTT from the IJ interval alone through the equation of the obtained line in subsequent measurements.

Figure 6:
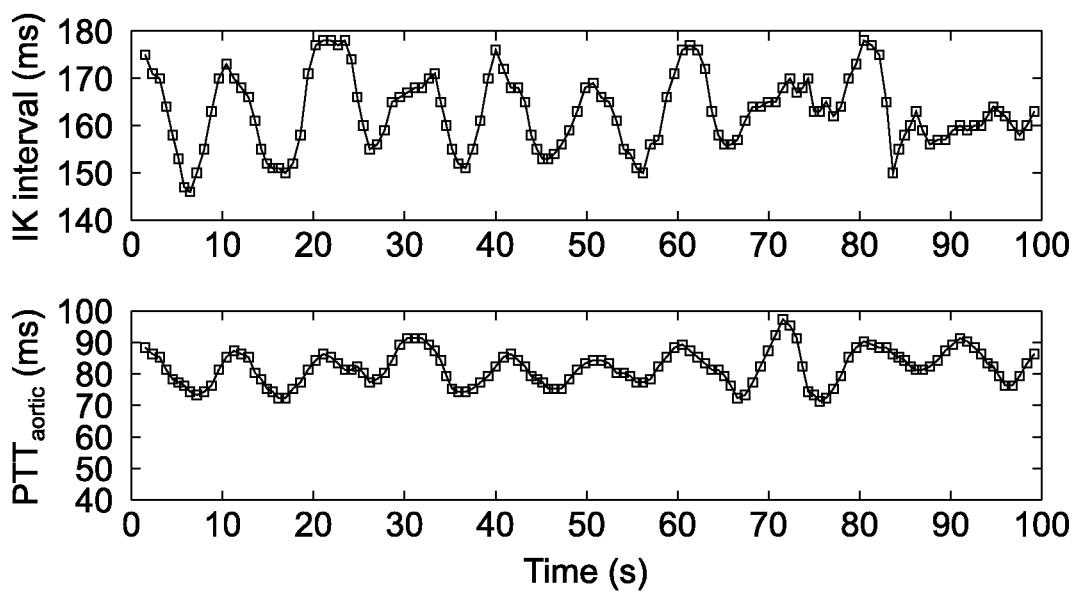
FIG. 6 shows an IK interval record of the BCG and a carotid-femoral PTT record simultaneously obtained from the same subject while he was performing a paced respiration maneuver in order to modulate arterial stiffness via respiratory-induced blood pressure variations.

FIG. 6 shows the data obtained in another preferred embodiment, in which the PTT is estimated from the interval between the minimum of wave I and the minimum of wave K, which is the so-called IK interval. The result is shown together with the carotid-femoral PTT measured simultaneously in the same subject during a paced respiration maneuver. As with the IJ interval in FIG. 4, the IK interval reflects the changes in the carotid-femoral PTT induced by the maneuver but are now increased because their duration is longer than that of the IJ interval, so that, in this embodiment, the carotid-femoral PTT is necessarily obtained from the calibration of the IK interval with respect to the carotid-femoral PTT measured with other means.

Once the invention has been sufficiently described, as well as three preferred embodiments, it should only be added that it is possible to make modifications in its constitution, materials used, and in the choice of the sensors used to obtain the BCG and the methods to identify the fiducial points of this BCG, without deviating from the scope of the invention, defined in the following claims.

What is claimed is:

1. A method for estimating the aortic pulse transit time (PTT) from a time interval measured between fiducial points of a ballistocardiogram (BCG), comprising:
    a) detecting, by a digital signal processing system, a first fiducial point in a BCG;
    b) detecting, by the digital signal processing system, a second fiducial point in the BCG that is latter to the first fiducial point and belongs to a same heartbeat;
    c) measuring, by a computing system, a time interval between said first and second fiducial points; and
    d) estimating an aortic PTT from said time interval measured between the two chosen fiducial points,
    wherein the estimated aortic PTT corresponds directly to the interval obtained between the detected fiducial points of the BCG, or
    wherein the estimated aortic PTT is obtained using a relationship between said aortic PTT and the time interval between two fiducial points of the BCG, said relationship being obtained through calibration of said time interval with respect to another method for obtaining the aortic PTT.

2. The method according to claim 1, wherein the first and second fiducial points of the BCG are detected by exclusively using the BCG.

3. The method according to claim 1, wherein the two fiducial points of the BCG are identified from an auxiliary cardiovascular signal.

4. The method according to claim 3, wherein:
    a heartbeat is detected from a R peak of an electrocardiogram and the two fiducial points of the BCG are detected within defined intervals from the R peak of the electrocardiogram, corresponding to the same heartbeat; or
    a heartbeat is detected from the foot of a pulse wave of a photoplethysmogram or a impedance plethysmogram and the two fiducial points of the BCG are detected within defined intervals from the foot of said pulse wave within the same heartbeat.

5. The method according to claim 1, wherein the detected fiducial points of the BCG belong to the I and J waves.

6. The method according to claim 1, wherein the detected fiducial points of the BCG belong to the I and K waves.

7. The method according to claim 1, wherein the detected fiducial points of the BCG belong to the J and K waves.

8. The method according to claim 5, wherein the interval between BCG fiducial points is measured between a minimum of the I wave and a maximum of the J wave.

9. The method according to claim 6, wherein the interval between BCG fiducial points is measured between a minimum of the I wave and a minimum of the K wave.

10. The method according to claim 7, wherein the interval between BCG fiducial points is measured between a maximum of the J wave and a minimum of the K wave.

11. The method according to claim 1, wherein said calibration comprises the performance of a linear regression between the time interval measured between BCG fiducial points and the aortic PTT obtained by said another method, obtained from a photoplethysmogram.

12. An apparatus to automatically estimate the aortic pulse transit time (PTT) from the time interval between fiducial points of a ballistocardiogram (BCG), comprises:
    a) a digital signal processing system configured to automatically detect two fiducial points in a single heartbeat of a BCG;
    b) a computing system configured to calculate a time interval between said two fiducial points and to estimate an aortic PTT from the calculated time interval, wherein the estimated aortic PTT corresponds directly to the interval obtained between the detected fiducial points of the BCG or the aortic PTT is obtained using a relationship between said aortic PTT and the time interval between two fiducial points of the BCG, said relationship being obtained through calibration of said time interval with respect to another method for obtaining the aortic PTT; and
    c) a communication system configured to communicate the estimated aortic PTT to an user or to another apparatus.

13. The apparatus according to claim 12, further comprising, additionally, a second computing system configured to obtain the aortic PTT from the said time interval.

14. The apparatus according to claim 12, comprising an input for an auxiliary cardiovascular signal and a unit to determine an extreme value in the BGC signal after a reference point in said auxiliary signal.

15. The apparatus according to claim 14, wherein the auxiliary cardiovascular signal is an impedance plethysmogram, a photoplethysmogram, or an electrocardiogram.

* * * * *